(12) United States Patent
Bartl et al.

(10) Patent No.: US 10,028,718 B2
(45) Date of Patent: Jul. 24, 2018

(54) ACCELERATED DATA CAPTURE IN AN X-RAY SYSTEM

(71) Applicants: Peter Bartl, Erlangen (DE); Anna Jerebko, Hausen (DE); Tom Weidner, Erlangen (DE)

(72) Inventors: Peter Bartl, Erlangen (DE); Anna Jerebko, Hausen (DE); Tom Weidner, Erlangen (DE)

(73) Assignee: Siemens Aktiengesellschaft, München (DE)

( * ) Notice: Subject to any disclaimer, the term of this patent is extended or adjusted under 35 U.S.C. 154(b) by 105 days.

(21) Appl. No.: 14/958,038

(22) Filed: Dec. 3, 2015

(65) Prior Publication Data

US 2016/0157804 A1    Jun. 9, 2016

(30) Foreign Application Priority Data

Dec. 3, 2014   (DE) .................. 10 2014 224 743

(51) Int. Cl.
| | | |
|---|---|---|
| G06K 9/00 | (2006.01) | |
| A61B 6/03 | (2006.01) | |
| A61B 6/00 | (2006.01) | |
| A61B 6/02 | (2006.01) | |

(52) U.S. Cl.
CPC ............ *A61B 6/5205* (2013.01); *A61B 6/025* (2013.01); *A61B 6/4233* (2013.01); *A61B 6/502* (2013.01); *A61B 6/54* (2013.01); *A61B 6/542* (2013.01); *A61B 6/58* (2013.01)

(58) Field of Classification Search
CPC ....... A61B 6/032; A61B 6/027; A61B 6/5205; A61B 6/06; G06T 11/005; G06T 11/006; G06T 2211/424; Y10S 378/901

USPC ............................................ 378/901, 4, 162
See application file for complete search history.

(56) References Cited

U.S. PATENT DOCUMENTS

| | | |
|---|---|---|
| 6,792,068 B1 | 9/2004 | Flohr et al. |
| 2006/0269041 A1 | 11/2006 | Mertelmeier |
| 2013/0028500 A1* | 1/2013 | Takahashi ............ A61B 6/032 |
| | | 382/132 |

FOREIGN PATENT DOCUMENTS

| | | |
|---|---|---|
| DE | 19935093 A1 | 2/2001 |
| DE | 102005022899 A1 | 11/2006 |

OTHER PUBLICATIONS

German Office action for related German Application No. 10 2014 224 743.8, dated Jul. 9, 2015, with English Tranlsation.

* cited by examiner

*Primary Examiner* — Don Wong
(74) *Attorney, Agent, or Firm* — Lempia Summerfield Katz LLC

(57) ABSTRACT

Data of a predetermined volume portion of an object under examination is captured by an x-ray system that includes an x-ray source and a detector. The x-ray source is activated to generate x-rays that emerge from the x-ray source, radiate through the volume portion, and after radiating through, impinge on the detector. X-rays impinging on the detector are captured pixel by pixel, in order to capture the data of the predetermined volume portion. With the pixel-by-pixel capture, only a subset of all the pixels of the detector is evaluated.

17 Claims, 3 Drawing Sheets

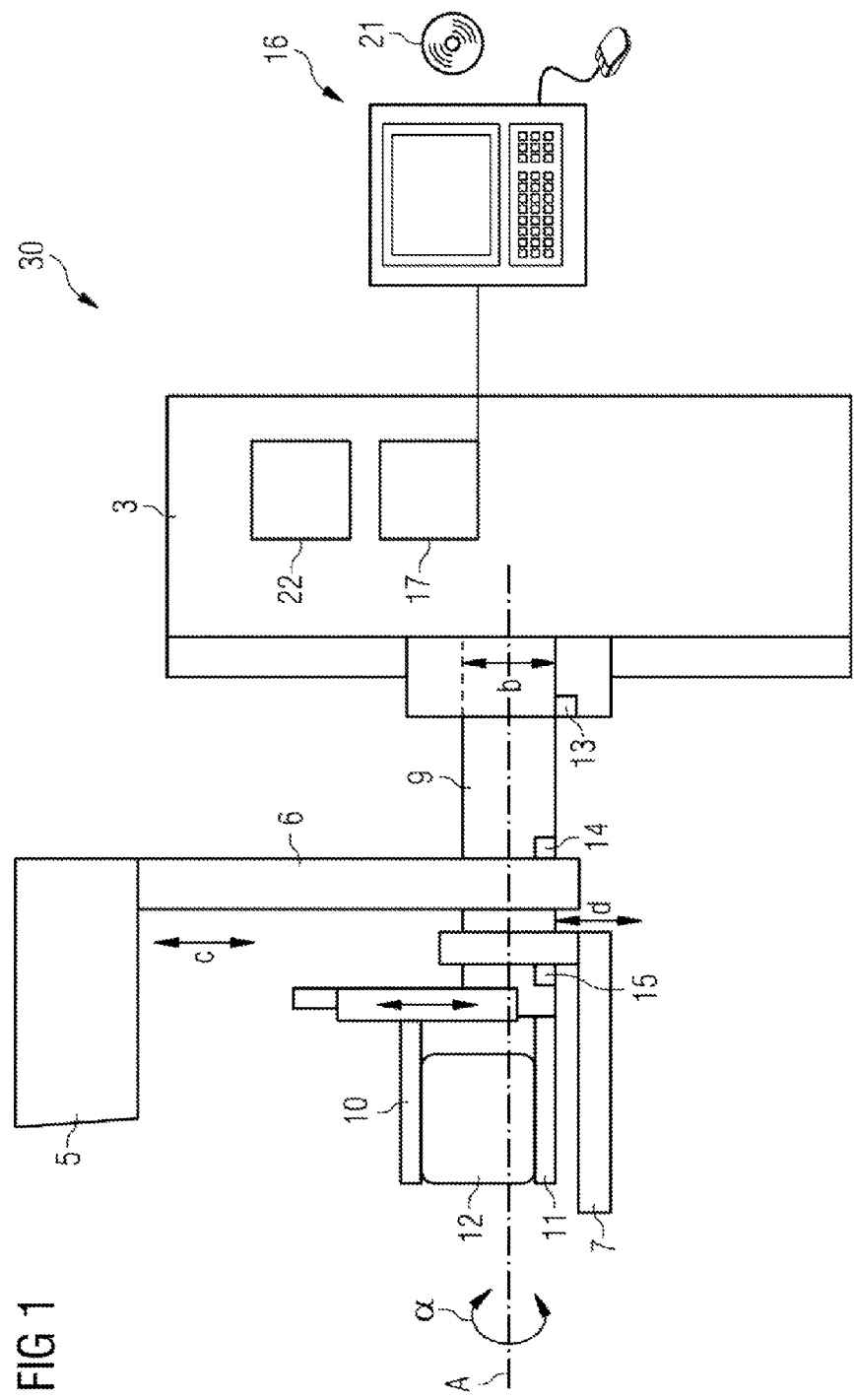

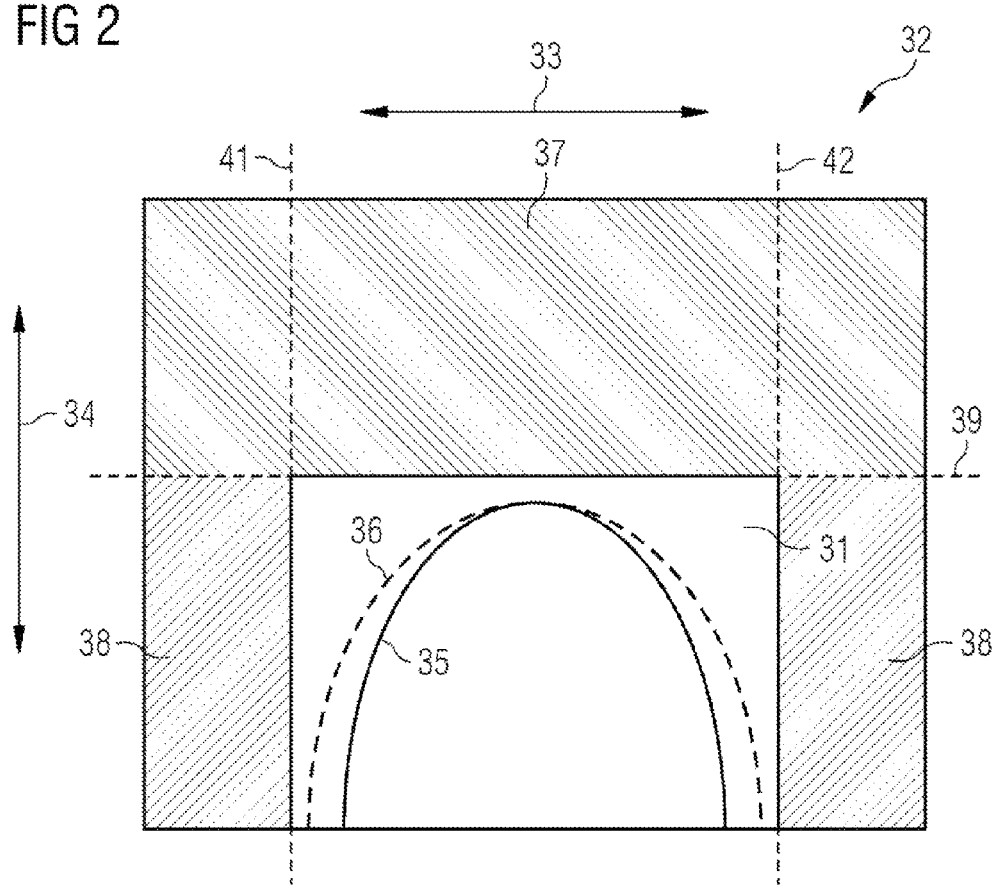

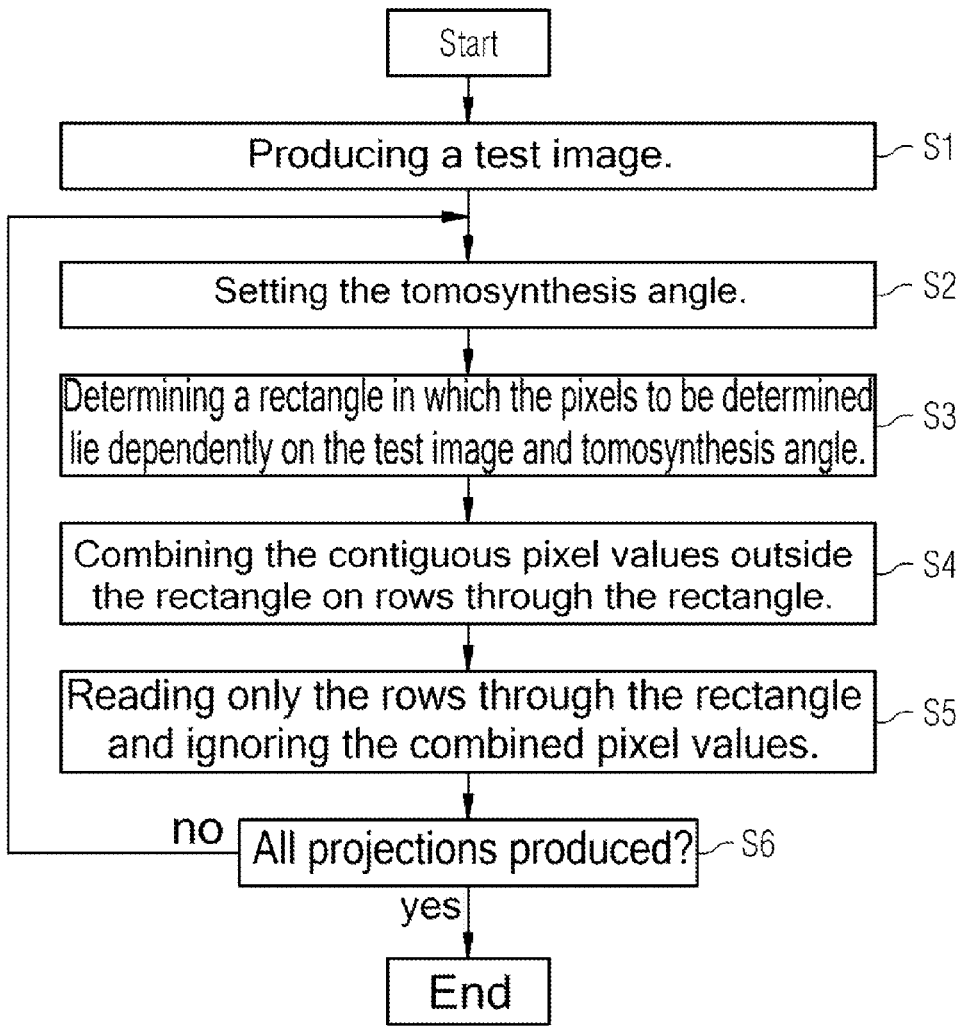

ACCELERATED DATA CAPTURE IN AN X-RAY SYSTEM

This application claims the benefit of DE 10 2014 224 743.8, filed on Dec. 3, 2014, which is hereby incorporated by reference in its entirety.

BACKGROUND

The present embodiments relate to accelerated data capture.

In the area of x-ray mammography, the significance of tomosynthesis has increased in recent years. In tomosynthesis, x-ray images are captured over a limited angular range. The projection images thereby determined may be reconstructed in the form of tomograms of any desired alignment. Often used as the x-ray detector for this is a flat field detector for mammography (FFDM) that represents a key component for the tomosynthesis. The data capturing time of the FFDM, and consequently the reading time for each projection image of the FFDM, is currently a very limiting factor with respect to the use of tomosynthesis.

In order to shorten the overall data capturing time in tomosynthesis, currently the number of projections captured is restricted. However, this approach has the great disadvantage that the available information about the object decreases with the number of projections captured. For example, the depth information of the reconstructed tomograms falls with the reduction in the number of projections. To sum up, the image quality of the tomosynthesis decreases with the reduction in the number of projections.

SUMMARY AND DESCRIPTION

The scope of the present invention is defined solely by the appended claims and is not affected to any degree by the statements within this summary.

The present embodiments may obviate one or more of the drawbacks or limitations in the related art. For example, the data capturing time in tomosynthesis is shortened without the image quality being reduced as a result.

Within the scope of the present embodiments, a method for capturing data of a predetermined volume portion of an object under examination with the aid of a digital x-ray system is provided. In this case, the x-ray system includes an x-ray source and a detector. The method according to one or more of the present embodiments includes activating the x-ray source to generate x-rays that emerge from the x-ray source, radiate through the predetermined volume portion and subsequently impinge on the detector. The method also includes capturing pixel by pixel the x-rays impinging on the detector in order to capture the data of the predetermined volume portion. With the pixel-by-pixel capture of the x-rays impinging on the detector, only a certain set or subset of the set of all of the pixels of the detector is evaluated. In other words, not all of the pixels of the detector but only specific pixels are evaluated. These specific pixels that are to be evaluated are referred to hereinafter as the subset of pixels to be evaluated.

The fact that only some of the pixels of the detector for capturing the data are evaluated provides that the reading time of the detector may be advantageously shortened. As a result, the time period for detecting the data may be shortened in comparison with the prior art, without reducing the number of projections, and consequently the image quality.

According to an embodiment, a transmission test, in which x-rays emerging from the x-ray source pass through the predetermined volume portion and subsequently impinge on the detector, is carried out. The x-rays impinging on the detector are captured pixel by pixel and evaluated in order to determine the pixels that capture the x-rays that have previously passed through the volume portion. This act may also be referred to as segmentation (e.g., in tomosynthesis, as breast segmentation). The subset of the pixels to be evaluated is determined based on the pixels that are determined. In other words, the subset of the pixels to be evaluated includes the pixels that have captured the x-rays that have previously passed through the volume portion. In the transmission test, a kind of test image or test projection is produced, this test projection also being referred to as an automatic exposure control (AEC) pre-shot or first tomosynthesis projection.

In the case of an x-ray image or a projection, only the pixels of the detector on which an x-ray that has previously passed through the volume portion to be examined impinges contain information. The fact that the subset of the pixels to be evaluated includes all pixels with which this is the case provides that the subset of the pixels to be evaluated has the same information as the entire set of pixels of the detector. Therefore, the fact that only the subset of the pixels to be evaluated is evaluated provides that no information is lost in comparison with the prior art, in which all of the pixels of the detector are evaluated. As a result of this, the image quality is maintained in spite of a reduced capturing time.

As an alternative to the previously described transmission test with x-rays, the transmission test may be carried out with a camera that is fitted on the side of the x-ray source and with which an optical exposure of the predetermined volume portion in the direction of the detector is produced as the test image. Based on the optical exposure, the area covered over by the predetermined volume portion on the detector may be determined, whereby the subset of the pixels to be evaluated may be determined without x-rays having to be emitted for this purpose.

According to a further embodiment, a rectangle in which all of the pixels previously determined by the transmission test are located is determined. If the pixels of the detector are arranged in the form of multiple straight-running parallel rows, two opposite sides of the rectangle lie parallel to the rows of the detector. The two other sides of the rectangle are perpendicular to the rows of the detector and consequently run parallel to the columns of the detector. In the case of this embodiment, the subset of the pixels to be evaluated is determined dependently on the rectangle. In other words, the subset of the pixels to be evaluated is determined by the pixels that lie within the rectangle.

Instead of the rectangle, other two-dimensional forms (e.g., a polygon or a semicircle (may be provided in the case of tomography) may also be determined. Such a two-dimensional form or surface area may be determined based on the test image for each segmentation (e.g., based on a brightness threshold value). The subset of the pixels to be evaluated is then determined dependently on this specific surface area that is determined. In comparison with the rectangle, the subset of the pixels to be evaluated may be determined more exactly, which is advantageous in the case of novel flat detectors. In the case of these flat detectors, a high density of the circuitry and high level of logic of the circuitry have the effect that every pixel may be individually read or not read.

The reading of the pixel values of the individual pixels of the detector may be carried out row by row (e.g., in the case of FFDM). If the subset of the pixels to be evaluated is described in the form of a rectangle of which the sides lie parallel to the rows of the detector, the reading of the pixel values may be performed dependently on the rectangle.

For example, only the rows of the detector that run through the rectangle are read.

If only the rows of the detector that run through the rectangle are read, the rows of the detector that do not touch the rectangle are not read. If the subset of the pixels to be evaluated is only located in the rectangle, there is no pixel to be evaluated outside the rectangle, and consequently, also no pixel to be evaluated on a row that is not read.

In other words, it is possible to dispense with reading the rows outside the rectangle without restricting the image quality as a result, since no pixel to be evaluated is located outside the rectangle.

For determining the rectangle, the two rows of the detector that lie on the detector at the periphery of the set of the pixels determined by the transmission test may be determined. These two rows are referred to hereinafter as peripheral rows. In a similar way, for determining the rectangle, the two columns of the detector that lie on the detector at the periphery of the set of the pixels determined by the transmission test may be determined. The two columns are referred to hereinafter as peripheral columns. The rectangle may then be determined by the two peripheral columns and the two peripheral rows.

For example, the rectangle may be determined such that the two peripheral columns and the two peripheral rows define the four sides of the rectangle. However, the rectangle may also be defined as somewhat larger, in that at least one side of the rectangle is offset further to the outside with respect to the corresponding peripheral column or peripheral row. The rectangle thus also includes pixels that do not belong to the pixels determined by the transmission test, between the corresponding side of the rectangle and the corresponding peripheral row or peripheral column.

Such an extension of the rectangle has the advantage that, even in the event of a movement of the volume object during the actual data capture, all of the pixels that are acted upon by an x-ray that has passed through the volume portion lie within the rectangle, and are consequently read. In other words, such an extension of the rectangle offers a certain safety buffer. In addition, the geometrical imaging of the object on the detector changes during a tomosynthesis scan or a movement of the x-ray source. If the trajectory of the x-ray source is known, the rectangle (e.g., of minimal size) may be determined dependently on the test image and dependently on the trajectory such that every x-ray that is emitted by the x-ray source (e.g., no matter where the x-ray source is located on the trajectory) and passes through the predetermined volume portion nevertheless impinges on a pixel within the rectangle.

When reading, the pixel values that belong to neighboring pixels outside the rectangle may be combined into one pixel value within the detector. This allows, for example, the pixel values that belong to pixels outside the rectangle and lie on rows that run through the rectangle to be combined into one pixel value. This combined pixel value may be discarded after the reading.

In the case of certain detectors, it is not possible not to read pixel values of specific pixels of a row if at least one pixel of the row is to be read. However, it is possible to combine the pixel values of pixels lying together into one single pixel value. Since the reading time depends on the number of pixels to be read, the reading time may be advantageously shortened by combining the pixel values of pixels lying outside the rectangle.

Normally, the rows of the detector run horizontally, while the column drivers of the detector determine the vertical direction. In the event that a different definition of columns and rows applies in the case of a certain detector (e.g., if the rows run vertically), one or more of the present embodiments apply nonetheless. In this event, according to one or more of the present embodiments, the columns of the specific detector are regarded as the rows, and the rows are regarded as the columns. Even in the case of detectors in which the pixels are not arranged in a Cartesian manner but, for example, radially or hexagonally, one or more of the present embodiments may be used in principle. Even in the case of these detectors, the rectangle, for example, may be determined according to one or more of the present embodiments.

According to one or more of the present embodiments, multiple exposures or projections are produced, for example, an individual direction or angle setting in which the x-rays radiate through the volume portion being set for each of these projections. For capturing the data for the multiple projections, 3D dimensions or a 3D model of the volume portion (e.g., a thickness of the volume portion perpendicularly to the detector surface) may be determined in advance in order to determine the subset of the pixels to be evaluated dependently on the 3D dimensions of the volume portion.

The transmission test is generally carried out only for one direction of the x-rays or angle setting. In this case, the subset of the pixels to be evaluated depends not only on the corresponding angle setting but also on the 3D dimensions of the volume portion. These 3D dimensions or the 3D model may be determined based on the results of the transmission test and the thickness of the volume portion.

Two possibilities exist for the determination of the subset of the pixels to be evaluated for different angle settings:

According to the first possibility, the subset of the pixels to be evaluated is individually determined dependently on the angle setting and separately or individually determined dependently on the 3D dimensions for each projection.

According to the second possibility, the same subset of the pixels to be evaluated is determined for all projections. In this case, the subset of the pixels to be evaluated that is the same for all projections is a pixel superset that includes each individual subset of the pixels to be evaluated for each projection.

The first possibility offers the advantage that the smallest subset of the pixels to be evaluated is produced for each projection, so that the reading time for each projection is smaller than in the case of the second possibility. By contrast, the second possibility has the advantage that only one subset of the pixels to be evaluated is to be determined for all projections, so that no reconfiguration between the individual projections is to take place.

In addition, the subset of the pixels to be evaluated may also be determined dependently on a geometry of the x-ray system. In this case, the geometry of the x-ray system defines an arrangement of the detector in relation to an arrangement of the x-ray source dependently on the respective angle setting or direction in which the x-rays radiate through the volume portion.

For example, the position of the detector may be constant for all projections independently of the angle setting. However, there is also the possibility that the alignment of the detector changes dependently on the angle setting, so that for each angle setting, the x-rays respectively impinge perpendicularly on the detector. By taking into consideration the geometry of the x-ray system, the subset of the pixels to be evaluated may consequently be determined exactly.

Also provided within the scope of one or more of the present embodiments is an x-ray system that includes a detector and an x-ray source for the emission of x-rays directed at the detector. In this case, the x-ray system is configured such that an object under examination may be positioned between the x-ray source and the detector such that the x-rays pass through a predetermined volume portion of the object under examination before the x-rays impinge on the detector. Apart from the detector and the x-ray source, the x-ray system includes a controller for activating the x-ray source and the detector and an image computing unit in order to receive data of the predetermined volume portion captured by the detector and produce data of the predetermined volume portion. The detector is configured to capture pixel by pixel the x-rays impinging on the detector. In this case, pixel-by-pixel capture may be that the detector is capable of specifying for each pixel a pixel value that depends on the intensity of the x-rays impinging on the detector at the location of the pixel. The x-ray system is configured such that, with the pixel-by-pixel capture, the x-ray system is not to evaluate all of the pixels of the detector but only a subset of all of the pixels of the detector.

The advantages of the x-ray system according to one or more of the present embodiments correspond substantially to the advantages of the method that have previously been set out in detail, so that there is no need for such advantages to be repeated here.

According to one or more of the present embodiments, the x-ray system is configured to carry out a tomosynthesis, so that the x-ray system may also be referred to as a tomosynthesis machine.

One or more of the present embodiments describe a computer program product (e.g., a computer program or software) including a non-transitory computer-readable storage medium (e.g., instructions loaded into a memory of a programmable controller or a computing unit of an x-ray system). With this computer program product, all or various of the previously described embodiments of the method may be executed when the computer program product runs in the controller or control device of the x-ray system. In this case, the computer program product may use programming (e.g., libraries and auxiliary functions) in order to realize the corresponding embodiments of the method. In other words, the computer program product may be, for example, a computer program or software with which one of the embodiments of the method described above may be executed or that executes this embodiment. In this case, the software may be a source code (e.g., C++) that is still to be compiled (e.g., assembled) and linked or only is to be interpreted. Alternatively, the software may be an executable software code that, for execution, is only to be loaded into the corresponding computing unit.

One or more of the present embodiments disclose an electronically readable data carrier (e.g., a DVD, a magnetic tape, a memory card or a USB stick) on which electronically readable control information (e.g., software (cf. above)) is stored. When this control information (e.g., software) is read from the data carrier and stored in a controller or computing unit of an x-ray system, all of the embodiments of the previously described method may be carried out.

The reading time of a detector (e.g., of an FFDM) may be reduced by one or more of the present embodiments, since only part of an active surface area is read. Since, for example, in the case of a tomosynthesis scan, the volume portion of interest (e.g., the breast) covers over only part of the active area, all of the clinically relevant areas are nevertheless captured.

In the case of mammography, the reduction of the reading time according to one or more of the present embodiments allows a tomosynthesis scan to be carried out just as quickly as a two-dimensional screening. The fact that the set of data read is reduced in comparison with the prior art provides that the transmission time of the data and the storage space for storing the data may also be advantageously reduced.

BRIEF DESCRIPTION OF THE DRAWINGS

FIG. 1 shows a schematic representation of one embodiment of an x-ray system.

FIG. 2 shows an exemplary active area of a detector divided into areas.

FIG. 3 shows a flow diagram for carrying out a tomosynthesis scan according to an embodiment.

DETAILED DESCRIPTION

In FIG. 1, an x-ray system 30 for mammography examinations according to one or more of the present embodiments, which may also be referred to as a tomosynthesis machine, is schematically represented. The x-ray system 30 includes a carrying arm 9 that is mounted pivotably about a horizontally running axis A in a mounting (compare double-headed arrow or angle α). The mounting is arranged on a stand 3 and is vertically adjustable, as indicated by the double-headed arrow b. Arranged on the carrying arm 9 are an arm 6 provided with an x-ray source 5, an area detector 7 (e.g., FFDM) and a compression device including a compression plate 10 and a bearing plate 11. In FIG. 1, a female breast 12 compressed by the compression plate 10 and the bearing plate 11 is represented in a schematic way. The arm 6 is pivotable about the axis A in relation to the carrying arm 9, the detector 7 and the compression device 10, 11. For height adjustments and pivoting movements, electric motors 13 to 15 of the x-ray system 30 are provided. Between the x-ray source 5 and the compression device, an x-ray filter 1 is attached to the arm 6 in order to filter the x-rays emitted by the x-ray source 5 before the x-rays impinge on the object under examination 12.

Control of the x-ray system 30 is performed via an operator control device 16 of the x-ray system 30, which is connected to a controller 17 and an image computing unit 22 of the x-ray system 30. Using a DVD 21, certain methods (including the method according to one or more of the present embodiments) may be loaded into the controller 17 and the operator control device 16.

In FIG. 2, an active area 32 or a detector surface 32 of the detector 7 represented in FIG. 1 is schematically represented. This active area 32 has pixels that are arranged in a row direction 33 and a column direction 34.

For example, by producing a test image, the area 35 on the detector surface 32 that is formed by the pixels that are acted upon by an x-ray or on which the x-ray emerging from the x-ray source 5 and radiating through the breast or the volume portion 12 impinges may be determined. In this case, the area 35 exactly applies only for the angle α chosen for producing the test image.

The area 36 on the detector surface 32 includes, for example, the areas 35 for all of the tomosynthesis angles used during a tomosynthesis scan. In other words, the area 36 includes the pixels on which an x-ray emerging from the x-ray source 5 and radiating through the volume portion 12 impinges for any tomosynthesis angle used. Each pixel on which an x-ray that has previously radiated through the volume portion impinges for any of the predetermined tomosynthesis angles α lies within the area 36.

Starting from this area 36, a rectangle 31 is constructed. The sides of the rectangle 31 lie parallel to the row direction 33 and parallel to the column direction 34. The rectangle 31 includes the area 36 including a safety margin. The pixels lying within the rectangle 31 form the set of pixels to be evaluated, which is also referred to as the subset of the pixels to be evaluated. Since the female breast 12 rests on the detector surface 32 from one side, one side (e.g., the lower side in FIG. 2) of the rectangle is formed by a delimiting side of the detector surface 32. The other three sides of the rectangle 31 are formed by the delimiting lines 39, 41 and 42.

When reading the pixel values, according to one or more of the present embodiments, only the pixels within the rectangle 31 are captured or read. In order to realize this, the pixels in the area 37 (in FIG. 2) above the rectangle 31 are not captured, in that the associated rows are not read. In addition, the pixel values of the two areas 38 (in FIG. 2) to the right and left of the rectangle 31 are respectively combined into one pixel value. If these two areas 38 respectively have M pixels in row direction 33 and N pixels in column direction 34, then M*N pixel values are combined into one pixel value. In comparison with the prior art, according to which these M*N pixel values are read individually, an acceleration by a factor of M*N is obtained by the combination into just one pixel value provided by the present invention.

In FIG. 3, a flow diagram of a method according to one embodiment is represented.

In act S1, a test image or AEC pre-shot is produced in order to produce the subset of pixels to be evaluated or the rectangle 31 (see FIG. 2) from the test image or AEC pre-shot.

In act S2, a tomosynthesis angle α is set in order to produce an x-ray image or a projection based on x-rays that impinge on the female breast in the direction of the tomosynthesis angle α. Depending on the tomosynthesis angle α and the test image, the rectangle 31 in which the subset of the pixels to be evaluated lies is constructed. In this case, there is the possibility of constructing and using the same rectangle for all tomosynthesis angles α or individually constructing for each tomosynthesis angle α a rectangle that is adapted to the respective tomosynthesis angle α.

When reading the pixel values, in act S4, pixel values of pixels that lie contiguously outside the constructed rectangle on rows through the constructed rectangle are combined into just one single pixel value. In act S5, only the rows that run through the rectangle 31 are read. In act S4, combined pixel values are ignored or discarded after the reading.

If it is detected in act S6 that a projection has been produced for each required tomosynthesis angle, the method is ended. Otherwise, the method returns to act S2.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for capturing data of a predetermined volume portion of an object under examination by an x-ray system, the x-ray system comprising an x-ray source and a detector, the method comprising:
    generating x-rays that emerge from the x-ray source, radiate through the predetermined volume portion, and after radiating through, impinge on the detector, the generating comprising activating the x-ray source;
    capturing the data of the predetermined volume, the capturing of the data comprising capturing pixel by pixel the x-rays impinging on the detector, wherein with the pixel-by-pixel capture, only a subset of all of the pixels of the detector are evaluated; and
    determining a rectangle in which the determined pixels are arranged, the determining of the rectangle being dependent on a trajectory of the x-ray source,
    wherein the subset of the pixels to be evaluated is determined dependently on the rectangle, and
    wherein only rows of the detector that run through the rectangle are read, such that rows that do not run through the rectangle are not read.

2. The method of claim 1, further comprising carrying out a transmission test, in which x-rays from the x-ray source are produced, pass through the predetermined volume portion, and impinge on the detector;
    determining pixels that capture x-rays that have previously passed through the predetermined volume portion, the determining comprising capturing the x-rays impinging on the detector pixel by pixel and evaluating the captured x-rays; and
    determining the subset of the pixels to be evaluated dependently on the pixels that are determined.

3. The method of claim 2,
    wherein the pixels of the detector are arranged in the form of multiple straight-running parallel rows, and
    wherein two opposite sides of the rectangle are arranged parallel to the straight-running rows.

4. The method of claim 3, further comprising determining two peripheral rows and two peripheral columns of the detector that lie at the periphery of the determined pixels,
    wherein the rectangle is determined based on the peripheral rows and peripheral columns.

5. The method of claim 1, further comprising combining pixel values that belong to neighboring pixels outside the rectangle into one pixel value when reading, the one pixel value being discarded after the reading.

6. The method of claim 3, wherein the subset of the pixels to be evaluated corresponds to a set of pixels of the detector that are arranged within the rectangle.

7. The method of claim 1, further comprising producing multiple projections, a different direction in which the x-rays radiate through the predetermined volume portion being set for each of the projections,
    wherein three dimensional (3D) dimensions of the volume portion (12) are determined, and
    wherein the subset of the pixels to be evaluated is determined dependently on the 3D dimensions of the predetermined volume portion.

8. The method of claim 7, wherein, for each projection, the subset of the pixels to be evaluated is individually determined dependently on the direction in which the x-rays radiate through the predetermined volume portion for the respective projection, or
    wherein the same subset of the pixels to be evaluated is determined for all of the projections, the same subset of the pixels to be evaluated comprising each individual subset of the pixels to be evaluated of each projection.

9. The method of claim 7, wherein the subset of the pixels to be evaluated is determined dependently on a geometry of the x-ray system, the geometry of the x-ray system defining a position of the detector in relation to a position of the x-ray source for the respective direction in which the x-rays radiate through the predetermined volume portion.

10. An x-ray system comprising:
a detector;
an x-ray source operable to emit x-rays directed at the detector, an object under examination being positionable between the x-ray source and the detector such that the x-rays pass through a predetermined volume portion of the object under examination before the x-rays impinge on the detector;
a controller operable to activate the x-ray source and the detector; and
an image processor configured to:
    receive data of the predetermined volume portion captured by the detector;
    produce data of the predetermined volume portion, the detector being configured to capture pixel by pixel the x-rays impinging on the detector, wherein the image processor is configured, with the pixel-by-pixel capture, to evaluate only a subset of all of the pixels of the detector; and
    determine a rectangle in which the determined pixels are arranged, the determination of the rectangle being dependent on a trajectory of the x-ray source,
wherein the subset of the pixels to be evaluated is determined dependently on the rectangle, and
wherein only rows of the detector that run through the rectangle are read, such that rows that do not run through the rectangle are not read.

11. The x-ray system of claim 10, wherein the x-ray system is configured to carry out a tomosynthesis.

12. The x-ray system of claim 10, wherein the x-ray system is configured to carry out a transmission test, in which x-rays from the x-ray source are produced, pass through the predetermined volume portion, and impinge on the detector,
wherein the x-ray system is further configured to determine pixels that capture x-rays that have previously passed through the predetermined volume portion, the determination comprising capture of the x-rays impinging on the detector pixel by pixel and evaluation, by the image processor, of the captured x-rays, and
wherein the image processor is configured to determine the subset of the pixels to be evaluated dependently on the pixels that are determined.

13. A computer program product comprising a non-transitory computer-readable storage medium storing instructions executable by a programmable controller of an x-ray system to capture data of a predetermined volume portion of an object under examination by the x-ray system, the x-ray system comprising an x-ray source and a detector, the instructions comprising:
    generating x-rays that emerge from the x-ray source, radiate through the predetermined volume portion, and after radiating through, impinge on the detector, the generating comprising activating the x-ray source;
    capturing the data of the predetermined volume, the capturing of the data comprising capturing pixel by pixel the x-rays impinging on the detector, wherein with the pixel-by-pixel capture, only a subset of all of the pixels of the detector are evaluated; and
    determining a rectangle in which the determined pixels are arranged, the determining of the rectangle being dependent on a trajectory of the x-ray source,
wherein the subset of the pixels to be evaluated is determined dependently on the rectangle, and
wherein only rows of the detector that run through the rectangle are read, such that rows that do not run through the rectangle are not read.

14. In a non-transitory computer-readable storage medium storing instructions executable by a controller of an x-ray system to capture data of a predetermined volume portion of an object under examination by the x-ray system, the x-ray system comprising an x-ray source and a detector, the instructions comprising:
    generating x-rays that emerge from the x-ray source, radiate through the predetermined volume portion, and after radiating through, impinge on the detector, the generating comprising activating the x-ray source;
    capturing the data of the predetermined volume, the capturing of the data comprising capturing pixel by pixel the x-rays impinging on the detector, wherein with the pixel-by-pixel capture, only a subset of all of the pixels of the detector are evaluated; and
    determining a rectangle in which the determined pixels are arranged using a trajectory of the x-ray source,
wherein the subset of the pixels to be evaluated is determined dependently on the rectangle, and
wherein only rows of the detector that run through the rectangle are read, such that rows that do not run through the rectangle are not read.

15. The non-transitory computer-readable storage medium of claim 14, wherein the instructions further comprise:
    carrying out a transmission test, in which x-rays from the x-ray source are produced, pass through the predetermined volume portion, and impinge on the detector;
    determining pixels that capture x-rays that have previously passed through the predetermined volume portion, the determining comprising capturing the x-rays impinging on the detector pixel by pixel and evaluating the captured x-rays; and
    determining the subset of the pixels to be evaluated dependently on the pixels that are determined.

16. The non-transitory computer-readable storage medium of claim 15,
wherein the pixels of the detector are arranged in the form of multiple straight-running parallel rows, and
wherein two opposite sides of the rectangle are arranged parallel to the straight-running rows.

17. The non-transitory computer-readable storage medium of claim 16, wherein the instructions further comprise determining two peripheral rows and two peripheral columns of the detector that lie at the periphery of the determined pixels,
wherein the rectangle is determined based on the peripheral rows and peripheral columns.

* * * * *